US010712084B2

(12) United States Patent
Choi et al.

(10) Patent No.: US 10,712,084 B2
(45) Date of Patent: Jul. 14, 2020

(54) REFRIGERATOR

(71) Applicants: LG ELECTRONICS INC., Seoul (KR); PUKYONG NATIONAL UNIVERSITY INDUSTRY—UNIVERSITY COOPERATION FOUNDATION, Busan (KR)

(72) Inventors: Yuri Choi, Seoul (KR); Eunjeong Kim, Seoul (KR); Jeongyon Kim, Seoul (KR); Myungsuk Lee, Seoul (KR)

(73) Assignees: LG ELECTRONICS INC., Seoul (KR); PUKYONG NATIONAL UNIVERSITY INDUSTRY-UNIVERSITY COOPERATION FOUNDATION, Busan (KR)

(*) Notice: Subject to any disclaimer, the term of this patent is extended or adjusted under 35 U.S.C. 154(b) by 0 days.

(21) Appl. No.: 15/753,733

(22) PCT Filed: Aug. 10, 2016

(86) PCT No.: PCT/KR2016/008807
§ 371 (c)(1),
(2) Date: Feb. 20, 2018

(87) PCT Pub. No.: WO2017/034188
PCT Pub. Date: Mar. 2, 2017

(65) Prior Publication Data
US 2018/0238613 A1    Aug. 23, 2018

(30) Foreign Application Priority Data

Aug. 21, 2015  (KR) .................. 10-2015-0117849

(51) Int. Cl.
F25D 27/00    (2006.01)
A61L 2/08     (2006.01)
(Continued)

(52) U.S. Cl.
CPC ............ *F25D 27/005* (2013.01); *A61L 2/084* (2013.01); *A61L 9/18* (2013.01); *F25D 17/042* (2013.01);
(Continued)

(58) Field of Classification Search
CPC ........ F25D 27/005; F25D 27/00; A61L 2/084; A61L 9/18; F21D 17/042
See application file for complete search history.

(56) References Cited

U.S. PATENT DOCUMENTS

2012/0201714 A1* 8/2012 Hashimoto .......... B01J 23/6527
422/22
2014/0245771 A1    9/2014 Kim et al.
(Continued)

FOREIGN PATENT DOCUMENTS

CN    2589913        12/2003
CN    2589913 Y  *  12/2003   ........... F25D 17/042
(Continued)

OTHER PUBLICATIONS

International Search Report and Written Opinion dated Nov. 22, 2016 issued in Application No. PCT/KR2016/008807 (Full English Text).
(Continued)

*Primary Examiner* — Anh T Mai
*Assistant Examiner* — Nathaniel J Lee
(74) *Attorney, Agent, or Firm* — KED & Associates LLP

(57) ABSTRACT

A refrigerator according to an embodiment of the present invention includes a sterilizing device, wherein the sterilizing device includes a light source assembly which emits visible rays, and a photocatalytic filter which reacts with the visible rays, and the light source assembly is disposed to be inclined at a predetermined angle with respect to a horizontal line equally dividing the photocatalytic filter in a case.

18 Claims, 8 Drawing Sheets

(51) Int. Cl.
*A61L 9/18* (2006.01)
*F25D 17/04* (2006.01)

(52) U.S. Cl.
CPC .......... *F25D 27/00* (2013.01); *A61L 2209/14* (2013.01); *F25D 2317/0415* (2013.01); *F25D 2317/0417* (2013.01)

(56) References Cited

U.S. PATENT DOCUMENTS

2014/0368103 A1   12/2014  Son et al.
2015/0033784 A1*  2/2015  Park ........................ F25D 11/00
                                                                                  62/264

FOREIGN PATENT DOCUMENTS

| EP | 2 765 372 | 8/2014 | |
|---|---|---|---|
| JP | 2004-166996 | 6/2004 | |
| JP | 2008-292146 | 12/2008 | |
| JP | 2008292146 A * | 12/2008 | |
| JP | 2008292146 A * | 12/2008 | |
| KR | 20-0466934 | 5/2013 | |
| KR | 10-2015-0014815 | 2/2015 | |
| WO | WO 2008/132817 | 11/2008 | |
| WO | WO-2012091256 A1 * | 7/2012 | ............. G01G 19/52 |

OTHER PUBLICATIONS

European Search Report dated Apr. 25, 2019 issued in EP Application No. 16839477.3.

\* cited by examiner

[Fig. 1]
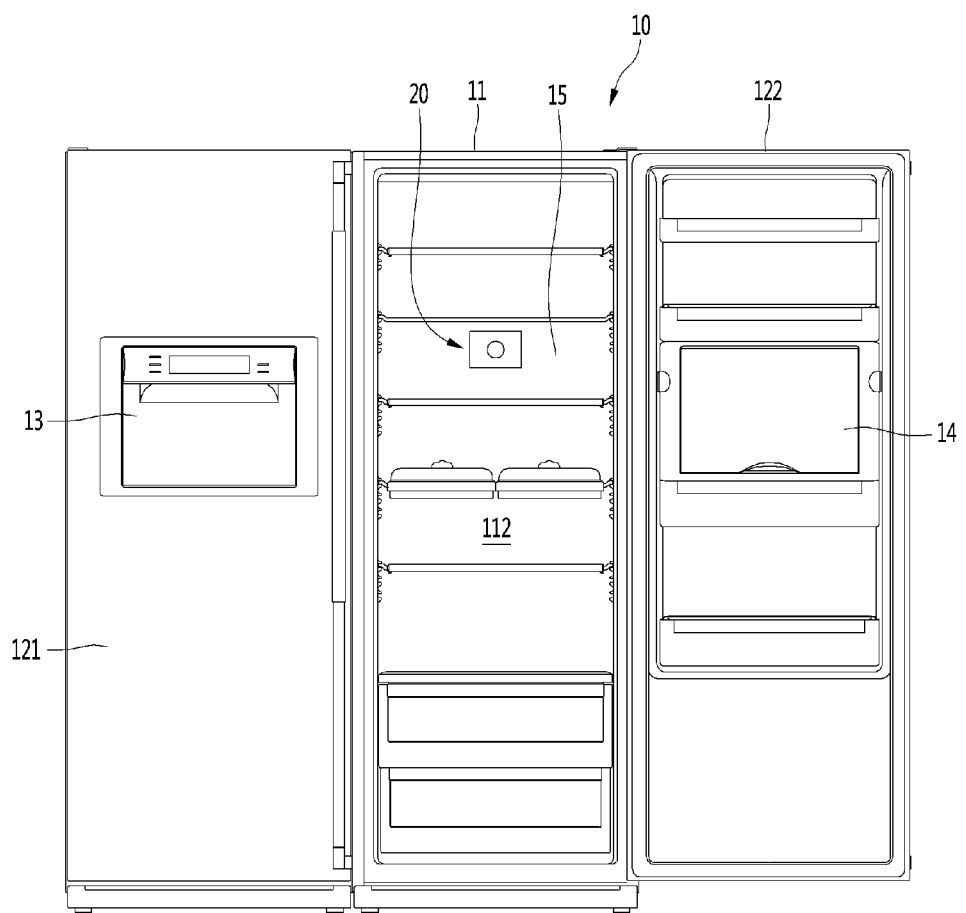

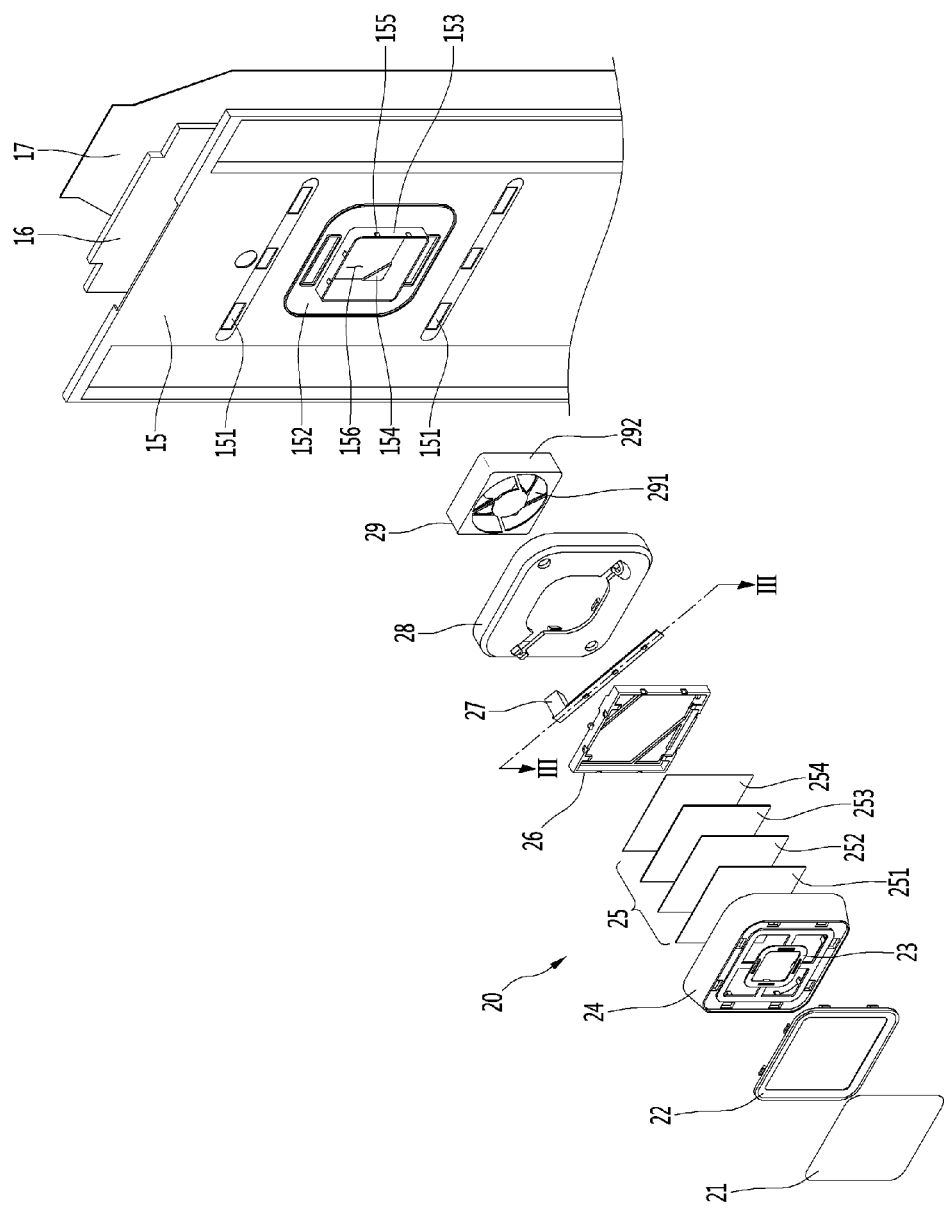
[Fig. 2]

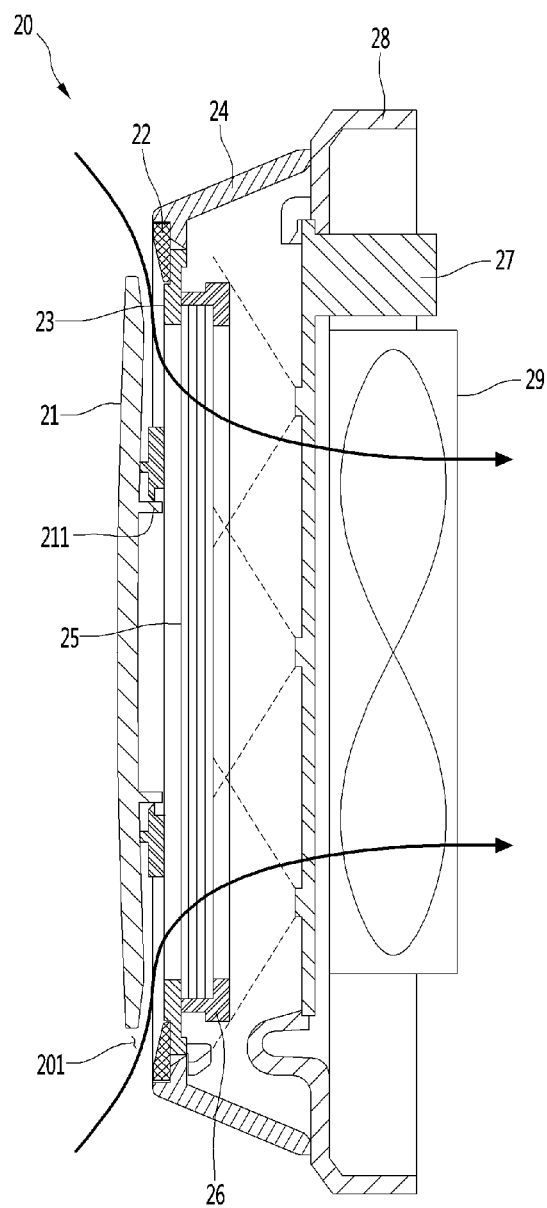

[Fig. 4]
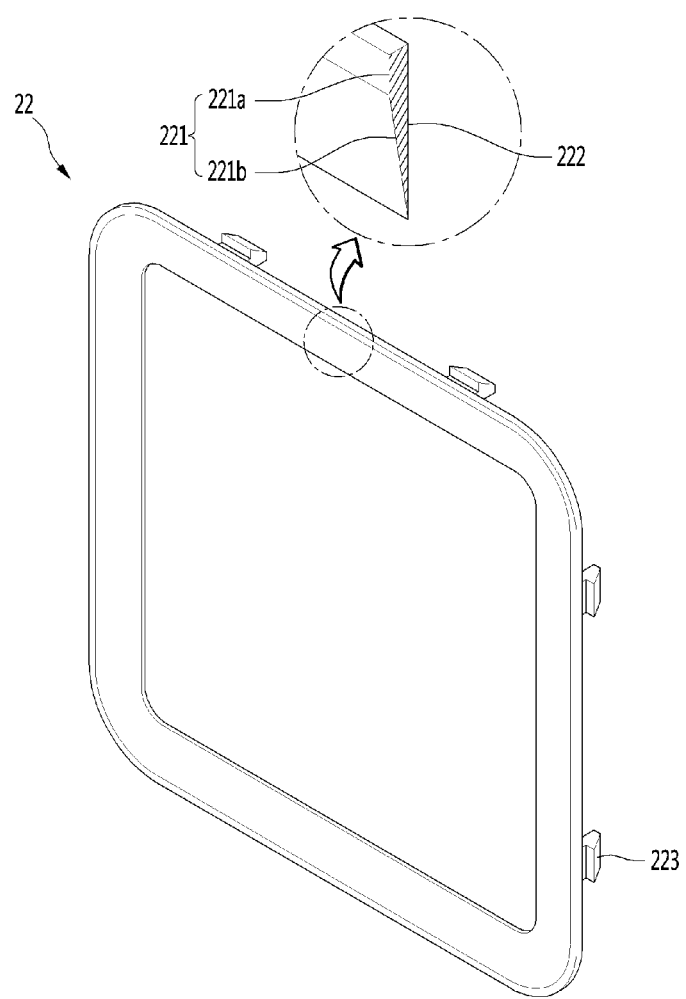

[Fig. 5]
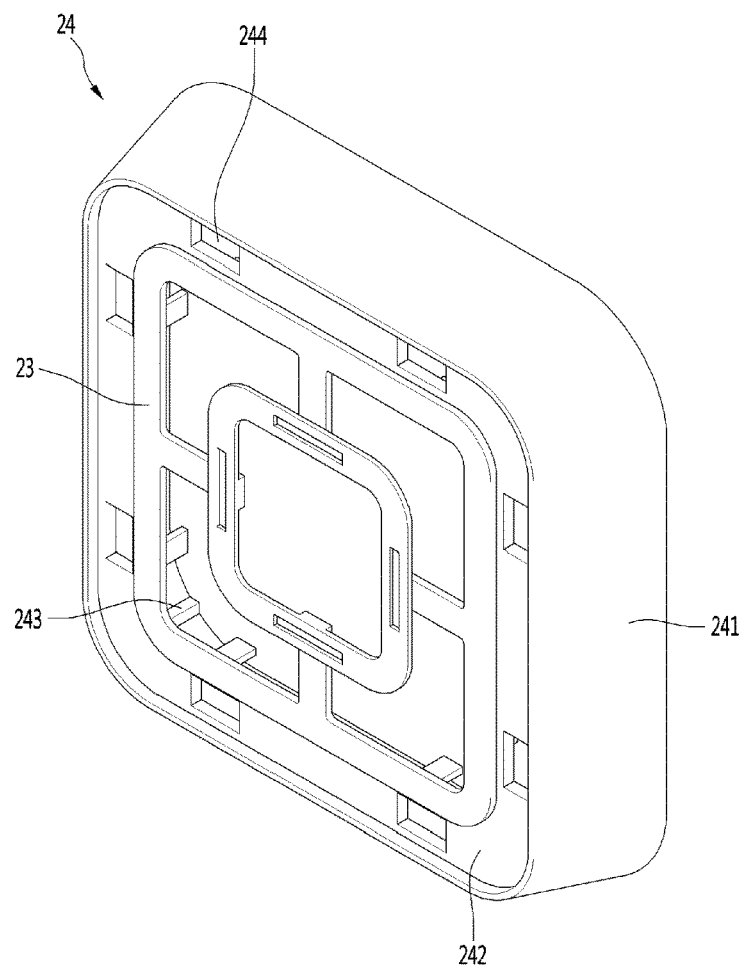
[Fig. 6]
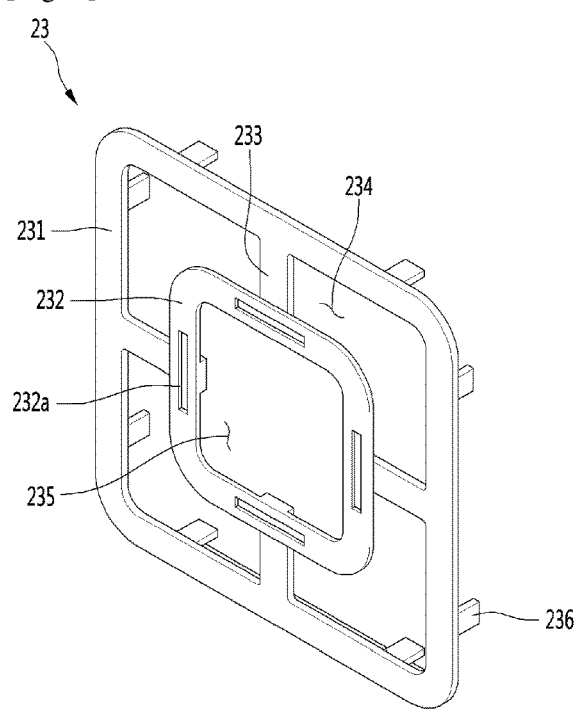

[Fig. 7]
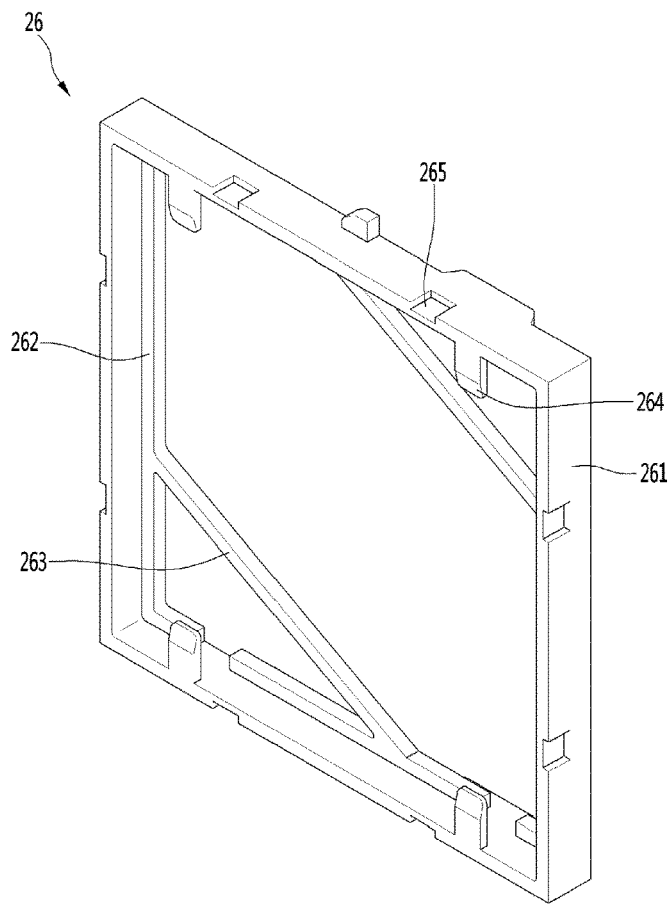
[Fig. 8]
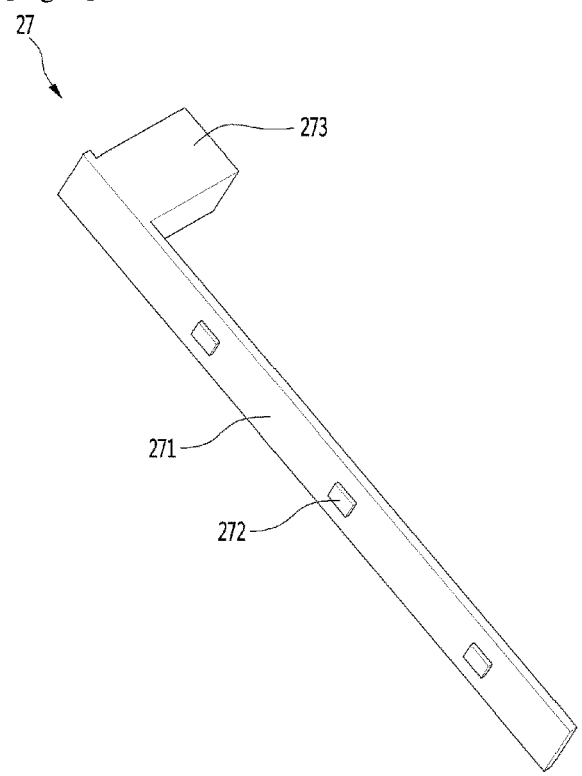

[Fig. 9]
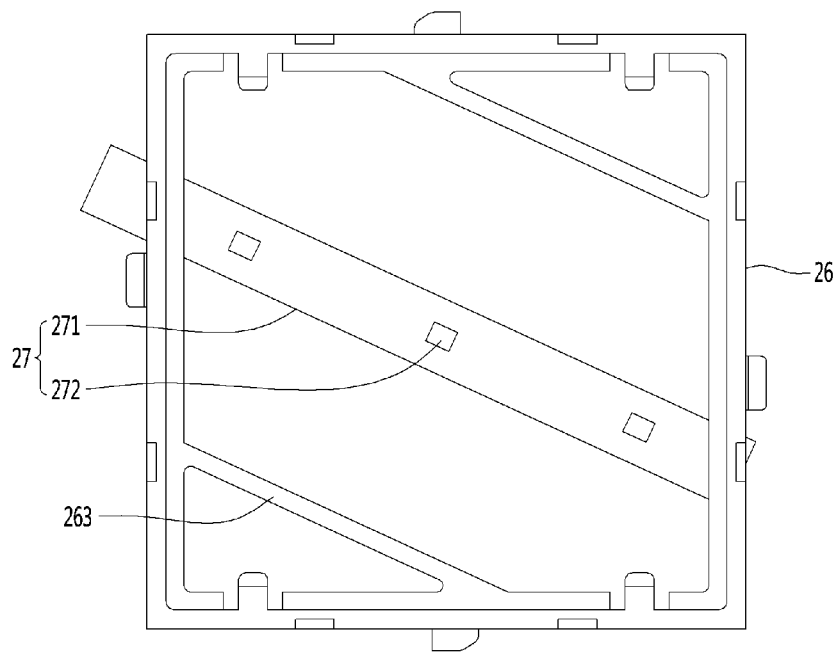
[Fig. 10]
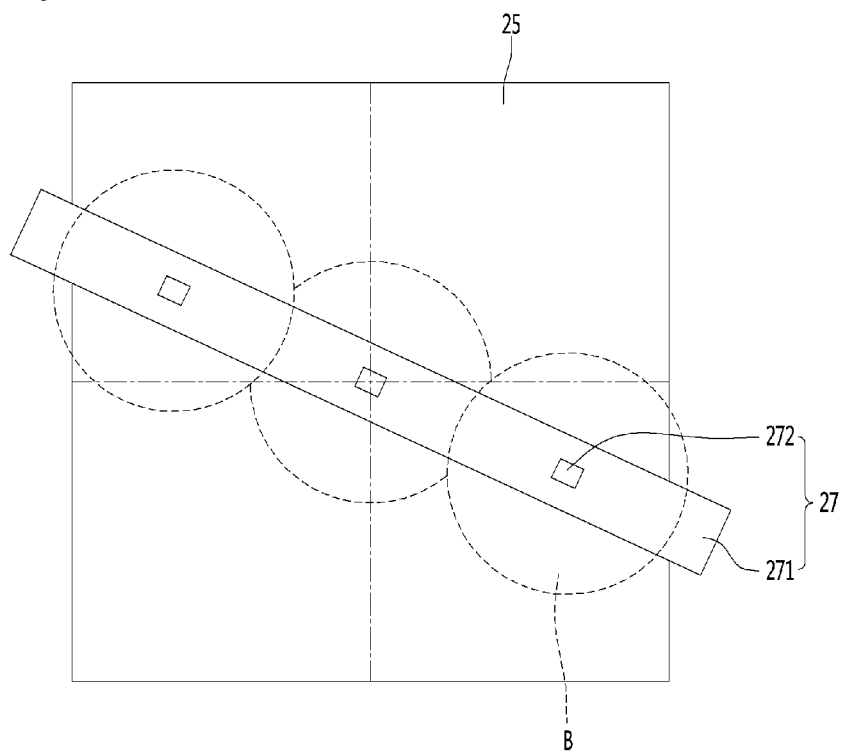

[Fig. 11]
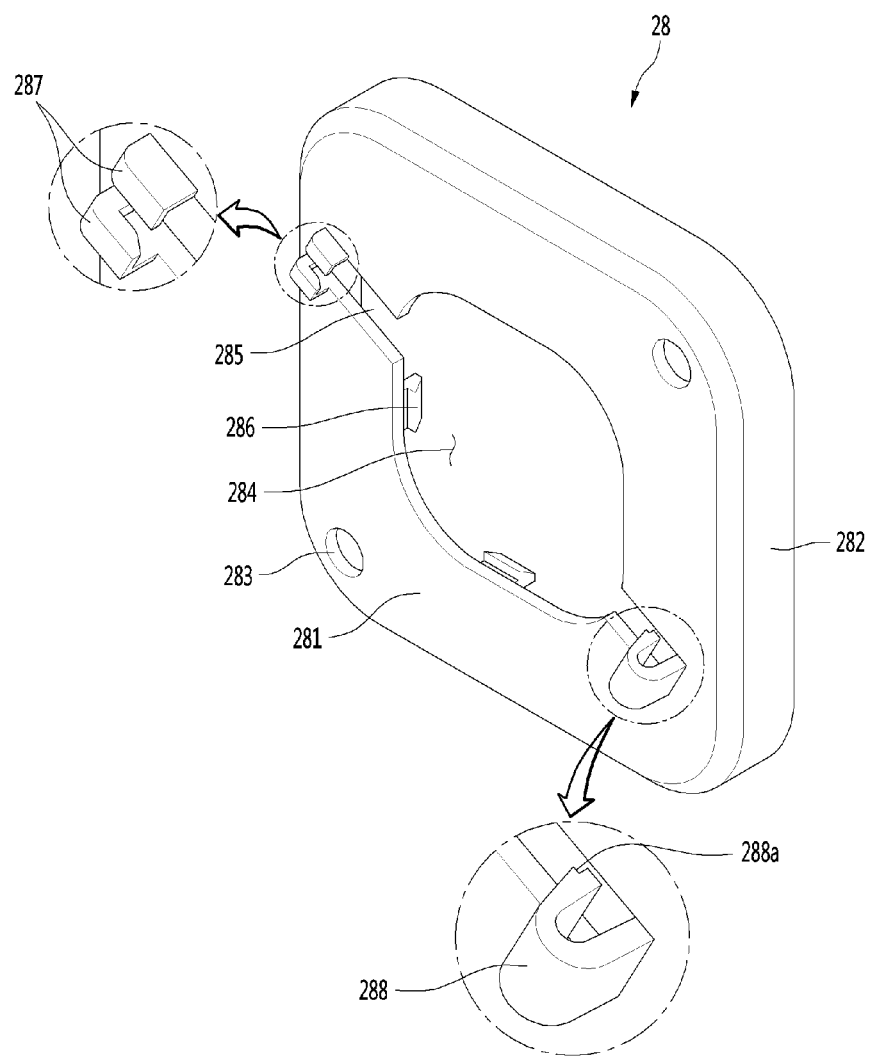

REFRIGERATOR

CROSS-REFERENCE TO RELATED PATENT APPLICATIONS

This application is a U.S. National Stage Application under 35 U.S.C. § 371 of PCT Application No. PCT/KR2016/008807, filed Aug. 10, 2016, which claims priority to Korean Patent Application No. 10-2015-0117849, filed Aug. 21, 2015, whose entire disclosures are hereby incorporated by reference.

TECHNICAL FIELD

The present invention relates to a refrigerator.

BACKGROUND ART

A refrigerator is a home appliance which keeps food refrigerated or frozen for a long time, and a device for curbing activity of many harmful microbes which may spoil food, or removing the microbes is required in the refrigerator.

That is, an air purifying filter or the like may be installed to remove harmful bacteria contained in cooling air inside a refrigerator compartment or a freezer compartment, and a sterilizing element which fits a kind, a size and a biological characteristic of a removal target should be included in the air purifying filter.

In a related art, there had been proposed a filter assembly in which a plurality of filters for deodorization and sterilization in a storage compartment are arranged to be overlapped with each other, and each of the filters is coated with biological and chemical elements including various sterilizing elements.

Also, there has been proposed a sterilizing device in which a light source emitting ultraviolet rays, and a photocatalytic filter which performs a sterilizing function using the ultraviolet rays in a certain wavelength range as a catalyst are installed.

According to Korean Patent Publication No. 10-2013-0015016 which was filed by the applicant, it may be understood that a photocatalytic filter using an LED light source emitting the ultraviolet rays in a wavelength range of 256 nm is employed.

However, in the case of the sterilizing device using the conventional UV photocatalytic filter, there are some disadvantages that the LED light source is expensive, and also is not supplied smoothly.

Also, in the case of the conventional UV photocatalytic filter, there are some problems that the ultraviolet rays are not evenly spread to the entire photocatalytic filter, and a portion of the filter at which a photocatalytic reaction does not occur is generated, and thus the sterilizing function is degraded.

DISCLOSURE OF INVENTION

Technical Problem

The present invention is directed to providing a refrigerator which is able to solve the above-described problems.

Solution to Problem

One aspect of the present invention provides a refrigerator including a sterilizing device, wherein the sterilizing device includes a light source assembly which emits visible rays, and a photocatalytic filter which reacts with the visible rays, and the light source assembly is disposed to be inclined at a predetermined angle with respect to a horizontal line equally dividing the photocatalytic filter in a case.

Advantageous Effects of Invention

The refrigerator having the sterilizing device according to the embodiment of the present invention having the above-described configuration has the following effects.

First, since the visible ray LED emitting the visible rays having a wavelength range of 400 to 800 nm is used as the photocatalytic filter, a high-efficient sterilizing effect can be obtained with a low cost.

Second, since the plurality of light sources are disposed at the predetermined interval, and the light sources are disposed in a diagonal direction of the filter assembly, the visible rays emitted from the light sources are evenly radiated to the entire area of the photocatalytic filter, and thus the sterilizing effect can be maximized.

Third, since a gap between the deodorizing filters disposed between the photocatalytic filters is selected appropriately so that the visible rays emitted from the light sources can sufficiently reach the forefront photocatalytic filter, the sterilizing effect can be increased.

Fourth, since the chip-on-board type LED elements are used as the light emitting elements, a wider light emitting angle than that of a bulb type LED can be ensured, and the visible rays can be evenly radiated to the entire area of the photocatalytic filter.

BRIEF DESCRIPTION OF DRAWINGS

FIG. 1 illustrates a front view of a refrigerator having a sterilizing device according to an embodiment of the present invention.

FIG. 2 is an exploded perspective view of a storage compartment in which the sterilizing device according to the embodiment of the present invention is installed.

FIG. 3 is a cross-sectional view taken along III-III of FIG. 2.

FIG. 4 is a perspective view of a guide ring forming the sterilizing device according to the embodiment of the present invention.

FIG. 5 is a perspective view of a front case forming the sterilizing device according to the embodiment of the present invention.

FIG. 6 is a perspective view of a front frame forming the sterilizing device according to the embodiment of the present invention.

FIG. 7 is a perspective view of a rear frame forming the sterilizing device according to the embodiment of the present invention.

FIG. 8 is a perspective view of a light source module forming the sterilizing device according to the embodiment of the present invention.

FIG. 9 is a view illustrating an arrangement state of the rear frame and the light source module.

FIG. 10 is a view illustrating light distribution of visible rays emitted from the light source module to a filter unit.

FIG. 11 is a perspective view of a rear case forming the sterilizing device according to the embodiment of the present invention.

MODE FOR THE INVENTION

Hereinafter, a refrigerator having a sterilizing device according to an embodiment of the present invention will be described in detail with reference to the accompanying drawings.

FIG. 1 illustrates a front view of a refrigerator having a sterilizing device according to an embodiment of the present invention.

Referring to FIG. 1, a refrigerator 10 according to an embodiment of the present invention may include a cabinet 11 in which a storage compartment is provided, and a door which is connected to the cabinet 11 to open and close the storage compartment, and a refrigeration cycle which cools the storage compartment.

Specifically, the storage compartment may include a freezer compartment which keeps food frozen, and a refrigerator compartment 112 which keeps the food refrigerated. And the door may include a freezer compartment door 121 which opens and closes the freezer compartment, and a refrigerator compartment door 122 which opens and closes the refrigerator compartment 112.

Also, a sterilizing device 20 according to an embodiment of the present invention may be installed at a duct cover 15 forming a rear surface of the refrigerator compartment 112. The sterilizing device 20 may be installed at not only the refrigerator compartment but also the freezer compartment.

Hereinafter, a configuration and a function of the sterilizing device 20 will be described in detail with reference to the drawings.

FIG. 2 is an exploded perspective view of the storage compartment in which the sterilizing device according to the embodiment of the present invention is installed, and FIG. 3 is a cross-sectional view taken along III-III of FIG. 2.

Referring to FIGS. 2 and 3, the storage compartment according to the embodiment of the present invention may include an inner case 17, a cooling air duct 16 which is installed at a front surface of the inner case 17, and a duct cover 15 which covers a front surface of the cooling air duct 16.

Specifically, the cabinet 11 includes the inner case 17, an outer case (not shown) which surrounds the inner case 17 and forms an exterior of the refrigerator 10, and a foaming material which is filled between the inner case 17 and the outer case.

Also, the cooling air duct 16 is a duct through which cooling air supplied from an evaporator chamber (not shown) for accommodating an evaporator flows, and the cooling air flowing through the cooling air duct 16 is discharged into the storage compartment.

Also, the duct cover 15 serves to cover the cooling air duct 16 and thus to enable the cooling air duct 16 not to be seen by a user. That is, the duct cover 15 substantially defines a rear wall surface of the storage compartment. And the duct cover 15 may include a sterilizing device installation portion at which the sterilizing device 20 is installed, and a plurality of cooling air discharge ports 151 through which the cooling air flowing through the cooling air duct 16 is discharged into the storage compartment. Here, the storage compartment may be a refrigerator compartment or a freezer compartment, and the embodiment is an example in which the storage compartment is a refrigerator compartment.

Specifically, the sterilizing device installation portion may include a rear case seating portion 152 at which a rear case (to be described later) forming the sterilizing device 20 is seated, a fan module support rib 153 which is formed inside the rear case seating portion 152 to support a fan module (to be described later) forming the sterilizing device 20, and a fan module seating rib 154 rib 154 is formed at a rear end of the fan module support rib 153 to prevent the fan module from being separated toward a rear of the duct cover 15. And a plurality of hooking protrusions 155 may be formed at an outer circumferential surface of the fan module support rib 153. A function of the hooking protrusions 155 will be described later. And a discharge hole 156 is formed inside the fan module support rib 153.

Meanwhile, the sterilizing device 20 may include at least a part or all of a front cover 21 which forms a front surface thereof, a front frame 23 which is coupled to a rear surface of the front cover, a front case 24 in which the front frame 23 is coupled to a front surface thereof, a guide ring 22 which surrounds an edge of the front surface of the front case 24, a rear case 28 which is coupled to a rear surface of the front case 24, a filter unit 25 which is located at a space formed by coupling between the front case 24 and the rear case 28 to purify the cooling air in the storage compartment, a rear frame 26 which supports a rear surface of the filter unit 25, and a fan module 29 which is disposed at a rear of the rear case 28 to suction the cooling air in the storage compartment.

Specifically, the fan module 29 may include a fan 291, and a fan housing 292 which surrounds the fan 291.

Also, a suction port 201 is formed between an edge of the front cover 21 and the edge of the front surface of the front case 24, and the cooling air in the storage compartment suctioned through the suction port 201 is guided by the guide ring 22, and purified while passing through the filter unit 25. The suction port 201 is formed in a band shape along an outer edge of the front cover 21.

Also, a plurality of fastening hooks 211 are formed to protrude from an edge of a rear surface of the front cover 21. The plurality of fastening hooks 211 may be hooked to the front frame 23. Since the front cover 21 is disposed at a front surface of the sterilizing device 20, internal elements of the sterilizing device 20 may be prevented from being exposed to a use's view when the storage compartment door is opened. Further, since the front cover 21 is disposed at the front surface of the sterilizing device 20, light emitted from a light source module 27 is prevented from being directly radiated to the user's eyes, and thus the user's glaring may be prevented.

Also, the filter unit 25 may have a structure in which a plurality of photocatalytic filters and a plurality of deodorizing filters are arranged forward and backward. Specifically, the filter unit 25 may include a first photocatalytic filter 251 through which the cooling air in the storage compartment suctioned through the suction port 201 passes first, a first deodorizing filter 252 and a second deodorizing filter 253 through which the cooling air passed through the first photocatalytic filter 251 passes in turn, and a second photocatalytic filter 254 through which the cooling air passed through the deodorizing filters passes finally.

The first photocatalytic filter 251 may be a prefilter which filters dust of 100 m or more, and is a sterilizing filter of which a surface is coated with a photocatalytic agent formed of a copper-titanium oxide ($CuTiO_2$), reacts with visible rays emitted from the light source module 27, and thus removes microbes contained in the cooling air. The first photocatalytic filter 251 may be a prefilter having a pore specification of $18*15/inch^2$, and a foreign substance having a relative large volume contained in the cooling air may be primarily filtered while passing through the first photocatalytic filter 251.

Also, the plurality of deodorizing filters 252 and 253 including activated carbon are disposed at a rear of the first photocatalytic filter 251, and remove odor contained in the cooling air primarily sterilized while passing through the first photocatalytic filter 251.

Also, each of the deodorizing filters 252 and 253 may have a pore specification of 9*7/inch$^2$. Since each of the deodorizing filters 252 and 253 has a relatively greater pore specification than that of the first photocatalytic filter 251, the visible rays emitted from the light source module 27 may be allowed to sufficiently reach the first photocatalytic filter 251. The installation number of the deodorizing filters 252 and 253 is not limited to the embodiment, and may be selected appropriately in consideration of a specification of the sterilizing device 20, required sterilizing ability and a specification of the light source module 27.

Also, the second photocatalytic filter 254 may be disposed at a rear of the second deodorizing filter 253. The cooling air sterilized and deodorized while passing through the deodorizing filters 252 and 253 is sterilized once more while passing through the second photocatalytic filter 254.

Specifically, like the first photocatalytic filter 251, the second photocatalytic filter 254 is also coated with the copper-titanium oxide. Since the second photocatalytic filter 254 is located just in front of the light source module 27, a nonwoven filter may be applied so that light emitted from the light source module 27 is radiated as much as possible. Further, in order to enable the visible rays to reach the first photocatalytic filter 251 located at the farthest side from the light source module 27, a nonwoven air filter may be applied. And the second photocatalytic filter 254 has an ability to remove harmful microbes including bacteria having a size of 2.5 m or more.

Also, a concentration of the photocatalytic agent coated on the first photocatalytic filter 251 may be different from that of the photocatalytic agent coated on the second photocatalytic filter 254. For example, since an amount of visible rays relatively smaller than that of visible rays radiated to the second photocatalytic filter 254 is radiated to the first photocatalytic filter 251, the concentration of the photocatalytic agent coated on the first photocatalytic filter 251 may be set lower than that of the photocatalytic agent coated on the second photocatalytic filter 254.

Hereinafter, each of elements forming the sterilizing device will be described in detail with reference to the drawings.

FIG. 4 is a perspective view of the guide ring forming the sterilizing device according to the embodiment of the present invention.

Referring to FIG. 4, the guide ring 22 of the sterilizing device 20 according to the embodiment of the present invention may be formed in a band shape having a predetermined width.

Specifically, the guide ring 22 may include a front surface portion 221 and a rear surface portion 222. The front surface portion 221 may include a non-inclined portion 221a which has a predetermined width from an outer edge of the guide ring 22 toward a center thereof, and an inclined portion 221b which has a width from an inner end of the non-inclined portion 221a to an inner edge of the guide ring 22.

The inclined portion 221b is formed so that the guide ring 22 is gradually inclined toward the rear surface portion 222 of the guide ring 22 in a direction toward the inner edge of the guide ring 22, and thus the cooling air in the storage compartment suctioned through the suction port 201 may be smoothly guided to the filter unit 25.

Also, a plurality of fastening hooks 223 protrude from a rear surface of the guide ring 22. The plurality of fastening hooks 223 may be inserted into the front surface of the front case 24. That is, the guide ring 22 may be fixed to and installed at the front surface of the front case 24 by the plurality of fastening hooks 223.

FIG. 5 is a perspective view of the front case forming the sterilizing device according to the embodiment of the present invention.

Referring to FIG. 5, the front case 24 of the sterilizing device 20 according to the embodiment of the present invention may include a side surface portion 241, and a guide ring seating portion 242 which is formed at a front surface of the side surface portion 241.

Specifically, the front frame 23 is put on the front surface of the front case 24. And as illustrated in the cross-sectional view of FIG. 3, a part of the guide ring 22 is seated on the guide ring seating portion 242, and the remaining part thereof is in contact with an edge of a front surface of the front frame 23. Therefore, the front cover 23 may be prevented by the guide ring 22 from being separated toward a front of the sterilizing device 20.

More specifically, the guide ring seating portion 242 is formed at a location which is spaced backward from a front end of the side surface portion 241 at a predetermined interval. Therefore, when the guide ring 22 is seated on the guide ring seating portion 242, a front surface of the guide ring 22 and the front end of the side surface portion 241 may be substantially located on the same plane.

Also, a plurality of guide ring fastening portions 244 are formed at the guide ring seating portion 242 in the form of grooves or holes, and the fastening hooks 223 of the guide ring 22 are inserted into the guide ring fastening portions 244.

Also, one or a plurality of fastening bosses 243 may be formed to extend from a rear surface of the guide ring seating portion 242 or an inner circumferential surface of the side surface portion 241.

FIG. 6 is a perspective view of the front frame forming the sterilizing device according to the embodiment of the present invention.

Referring to FIG. 6, the front frame 23 is located at the front surface of the front case 24 (referring to FIG. 5).

Specifically, the front frame 23 may include a band-shaped outer rib 231, a band-shaped inner rib 232 which is formed inside the outer rib 231, and a plurality of connection ribs 233 which connect the inner rib 232 with the outer rib 231.

Also, a plurality of fastening ends 236 may be formed to protrude from an edge of a rear surface of the outer rib 231. And a plurality of front cover fastening portions 232a may be formed at the inner rib 232 in the form of grooves or holes. And the fastening hooks 211 of the front cover 21 are inserted into the front cover fastening portions 232a, and thus the front cover 21 is fixed to the front frame 23.

And an outer suction port 234 is formed between the inner rib 232 and the outer rib 231. The outer suction port 234 may be divided into a plurality of suction ports by the connection ribs 233. And by forming the connection ribs 233 and the inner rib 232, the filter unit 25 may be prevented from being separated forward.

Also, a central suction port 235 is formed inside the inner rib 232.

FIG. 7 is a perspective view of the rear frame forming the sterilizing device according to the embodiment of the present invention.

Referring to FIG. 7, the rear frame 26 of the sterilizing device 20 according to the embodiment of the present invention may be fixed to a rear surface of the front frame 23.

Specifically, the rear frame 26 may include a frame body 261 which surrounds an edge of the filter unit 25, a plurality of fastening hooks 264 which extend from an inner edge of a front surface of the frame body 261 toward a center of the frame body 261, a filter seating portion 262 which extends from an inner edge of a rear surface of the frame body 261 in a predetermined width and enables the filter unit 25 to be seated thereon, and a separation preventing rib 263 which connects the adjacent filter seating portions 262.

More specifically, a fastening groove 265 may be formed at an outer circumferential surface thereof close to a front end of the frame body 261, and the fastening end 236 of the front frame 23 may be inserted into the fastening groove 265. In addition, the fastening hooks 264 may be hooked to an inner edge of the outer rib 231, and thus the rear frame 26 may be stably coupled to the front frame 23. And the filter unit 25 is accommodated in an internal space formed by coupling the front frame 23 with the rear frame 26.

Also, since the separation preventing rib 263 is formed at an edge side of the rear frame 26, the cooling air in the storage compartment passing through the filter unit 25 may be guided toward the fan module 29.

Furthermore, the separation preventing rib 263 does not extend vertically or horizontally, but extends to be inclined. This is to prevent the light emitted from the light source module 27 from being shielded because the light source module 27 is disposed to be inclined.

FIG. 8 is a perspective view of the light source module forming the sterilizing device according to the embodiment of the present invention, FIG. 9 is a view illustrating an arrangement state of the rear frame and the light source module, and FIG. 10 is a view illustrating light distribution of visible rays emitted from the light source module to a filter unit.

First, referring to FIG. 8, the light source module 27 according to the embodiment of the present invention may include a substrate portion 271, a plurality of light emitting elements 272 which are disposed on a front surface of the substrate portion 271 at a predetermined interval, and a control box 273 which is installed at an edge of a rear surface of the substrate portion 271.

The substrate portion 271 is not disposed in parallel with a horizontal side or a vertical side of the filter module 25, but is disposed to be inclined diagonally, and thus the light emitted from the light emitting elements 272 may be radiated to the second photocatalytic filter 254 as much as possible. This is because a sterilizing effect is maximized as a light distribution area of the light radiated to the second photocatalytic filter 254 is increased.

It is effective that the substrate portion 271 is inclined within an angular range of about 20 to 45 degrees with respect to the horizontal side of the filter module 25. Preferably, the substrate portion 271 may be disposed to be inclined at an angle of about 25 degree.

Also, the light emitting elements 272 may be LED elements which emit the visible rays having a wavelength of 400 to 700 nm. Preferably, they may be the LED elements which emit the visible rays having a wavelength of 400 to 450 nm.

Also, to equalize and maximize the light distribution, the LED light emitting elements 272 may be chip-on-board type LED light emitting elements which Lambertian-emit the visible rays.

Meanwhile, as illustrated in FIG. 10, as a distance between the filter and the light source is increased, it is advantageous in an aspect that the light distribution area is widened, but there are some disadvantages that an intensity of the visible rays reaching the photocatalytic filter becomes weak and an entire thickness of the sterilizing device 20 is increased. In consideration of the two factors, a proper distance between the filter and the light source may be 3 to 10 mm, preferably 9 mm. This has an advantage that the distance between the filter and the light source can be reduced further than that in an ultraviolet LED light source.

FIG. 11 is a perspective view of the rear case forming the sterilizing device according to the embodiment of the present invention.

Referring to FIG. 11, the rear case may include a front surface portion 281 which has a discharge port 284 formed therein, and a side surface portion 282 which extends backward along an outer edge of the front surface portion 281.

Specifically, a plurality of fastening hooks 286 may be formed to protrude from a rear surface of the front surface portion. The plurality of fastening hooks 286 may protrude from points adjacent to an edge of the discharge port 284.

Also, a fastening hole 283 may be formed at each of diagonal corners of the front surface portion 281 facing each other. And fastening members (not shown) may pass through the fastening holes 283, and then may be inserted into the fastening bosses 243 which protrude from the rear surface of the front case 24 corresponding to locations of the fastening holes 283. Then, the rear case 28 is fixed and coupled to the front case 24.

Also, a substrate seating portion 285 is formed to extend from the edge of the discharge port 284 toward the edge of the front surface portion 281. The substrate seating portion 285 may be formed to be recessed in a depth corresponding to a thickness of the substrate portion 271. When the substrate portion 271 is seated on the substrate seating portion 285, instead of being fixed to the boss protruding from the front surface portion 281, there is an advantage that the distance between the filter and the light source may be increased while the thickness of the sterilizing device 20 is not increased.

Also, it is natural that the substrate seating portion 285 extends to be inclined diagonally at the same angle as an inclined angle of the substrate portion 271.

Also, a substrate fixing rib 287 for fixing and supporting one end of the substrate portion 271 may be formed at one end of the substrate seating portion 285 to protrude and be bent. As illustrated in FIG. 3, one end of the substrate portion 271 may be fixed and supported by the substrate fixing rib 287, and thus the substrate portion 271 may be prevented from being separated forward.

Also, an elastic support rib 288 for fixing and supporting the other end of the substrate portion 271 may be formed to protrude from the other end of the substrate seating portion 285. As illustrated in the drawing, the elastic support rib 288 is curved in a U shape, and has a predetermined elastic force. And a catching portion 288a is formed at an extending end of the elastic support rib 288, and the other end of the substrate portion 271 is caught thereby.

Specifically, in order for the substrate portion 271 to be seated on the substrate seating portion 285, one end of the substrate portion 271 is inserted into the substrate fixing rib 287, and then pushed toward a rear of the sterilizing device 20. Then, the other end of the substrate portion 271 elastically deforms the elastic support rib 288 while being moved along an outer circumferential surface of the elastic support rib 288. And when the substrate portion 271 is moved to the catching portion 288*a*, the elastic support rib 288 is returned to an original state, and thus the other end of the substrate portion 271 is caught by the catching portion 288*a*, and not separated.

Also, the rear case 28 is seated on the rear case seating portion 152 formed at a front surface of the duct cover 15. At the same time, the fastening hooks 286 which protrude from a rear surface of the front surface portion 281 are caught by the hooking protrusions 155 protrusions 155 FIG. 2) which protrudes from an outer circumferential surface of the filter module support rib 153. Then, the rear case 28 is stably fixed to the fan module support rib 153.

An air flow in the sterilizing device 20 having such a configuration will be described. The cooling air in the storage compartment is suctioned through the suction port 201 formed along the outer edge of the front cover 21.

The suctioned cooling air is introduced into the filter unit 25 through cooling air suction ports formed at the front surface of the front case 24. And the cooling air introduced into the filter unit 25 is sterilized and deodorized while passing through the photocatalytic filter and the deodorizing filter. And the cooling air passed through the filter unit 25 passes through the rear case 28, and then is discharged to a rear of the fan module 29. And the cooling air discharged to the rear of the fan module 29 is guided inside the cooling air duct 16 through the discharge hole 156 hole 156 inside the fan module support rib 153 rib 153, the cooling air supplied from the evaporator chamber and flowing through the cooling air duct 16 and the cooling air passed through the sterilizing device 20 are mixed and then discharged again to the storage compartment.

Table 1 shows a result of a sterilizing performance experiment according to a type of an inorganic photocatalyst while a visual ray LED is used as the light source. As the result of the experiment, the order of the inorganic photocatalysts which have excellent sterilizing performance is as follows: Cu>Zn>Fe, Mn. Therefore, it is confirmed that an optimal type of the photocatalyst is Cu+$TiO_2$.

TABLE 1

| | | Blue LED | | White LED | |
|---|---|---|---|---|---|
| | | filter type | | | |
| Time | coating liquid type | Pre | non-woven | Pre | non-woven |
| 2 hr | Cu 2000 ppm + $TiO_2$ | 99.98% | 100% | 99.96% | 100% |
| | $Fe_2O_3$ 2000 ppm + $TiO_2$ | 90.55% | 100% | 91.59% | 100% |
| | Zn 2000 ppm + $TiO_2$ | 99.99% | 100% | 99.96% | 100% |
| | Mn(precursor_1) 2000 ppm + $TiO_2$ | 89.46% | 100% | 90.70% | 100% |
| | Mn(precursor_2) 2000 ppm + $TiO_2$ | 89.02% | 100% | 88.95% | 99.98% |
| 4 hr | Cu 2000 ppm + $TiO_2$ | 100% | 100% | 100% | 100% |
| | $Fe_2O_3$ 2000 ppm + $TiO_2$ | 99.81% | 100% | 99.67% | 100% |
| | Zn 2000 ppm + $TiO_2$ | 99.96% | — | 99.97% | — |
| | Mn(precursor_1) 2000 ppm + $TiO_2$ | 99.94% | — | 99.83% | — |
| | Mn(precursor_2) 2000 ppm + $TiO_2$ | 99.95% | | 99.88% | — |

Table 2 shows a result of an antimicrobial activity experiment of the prefilter coated with a single visible ray catalytic material with respect to *E. coli*.

In the result of the experiment, as shown in Table 2, it may be confirmed that the sterilizing performance of the Cu+$TiO_2$ photocatalytic filter is the most excellent.

TABLE 2

| | Experimental conditions | | | | | | | | | |
|---|---|---|---|---|---|---|---|---|---|---|
| | 2 hr | | | | 4 hr | | | | | |
| Classification | First | Second | Third | Average | First | Second | Third | Fourth | Fifth | Average |
| $TiO_2$ 25,000 ppm + Cu 2000 ppm | 99.99% | 99.99% | 99.95% | 99.98% | 100% | 100% | — | — | — | 100% |
| $TiO_2$ 25,000 ppm + Cu 1,500 ppm + Zn 500 ppm | 99.91% | 99.93% | — | 99.92% | 99.83% | 99.76% | 99.99% | 99.83% | 99.98% | 99.89% |
| $TiO_2$ 25,000 ppm + Cu 1,000 ppm + Zn 1,000 ppm | 99.83% | 99.57% | 99.39% | 99.60% | 100% | 99.65% | 99.95% | 99.92% | 100% | 99.88% |
| $TiO_2$ 25,000 ppm + Cu 500 ppm + Zn 1,500 ppm | — | — | — | — | 99.88% | 99.76% | — | — | — | 99.82% |
| $TiO_2$ 25,000 ppm + Mn(2) 2000 ppm | — | — | — | — | 91.88% | 58.85% | — | — | — | 75.35% |
| $TiO_2$ 25,000 ppm + Cu 1,500 ppm + Mn 500 ppm | 99.88% | 99.51% | — | 99.70% | 99.42% | 99.29% | — | — | — | 99.36% |
| $TiO_2$ 25,000 ppm + Cu 1,000 ppm + Mn 1,000 ppm | 99.67% | 97.47% | 99.92% | 99.02% | 95.21% | 98.24% | — | — | — | 96.73% |
| $TiO_2$ 25,000 ppm + Cu 500 ppm + Mn 1,500 ppm | 99.88% | 99.51% | — | 98.94% | — | — | — | — | — | — |

Table 3 shows a result of the antimicrobial activity experiment according to a concentration of a copper or zinc photocatalytic material, and it may be confirmed that the copper has more excellent antimicrobial activity than the zinc.

TABLE 3

|  | Classification | The number of experiments | | | | | |
|---|---|---|---|---|---|---|---|
|  |  | First | Second | Third | Fourth | Fifth | Average |
| TiO₂ +Cu 25,000 ppm | 2,000 ppm E. coli | 100% | 100% |  |  |  | 100% |
|  | S. aureus | 99.38% | 99.65% | 99.68% | 99.16% |  | 99.47% |
|  | S. typhimurium | 97.75% | 99.92% | 99.85% |  |  | 99.17% |
|  | K. pneumoniae | 96.96% | 99.98% | 99.98% |  |  | 98.97% |
|  | L. monocytogenes | 99.33% | 98.36% | 98.76% |  |  | 98.82% |
|  | 3,000 ppm E. coli | 100% | 100% |  |  |  | 100% |
|  | S. aureus | 99.96% | 99.91% | 99.66% | 98.58% | 99.29% | 99.48% |
|  | 4,000 ppm E. coli | 100% | 100% |  |  |  | 100% |
|  | S. aureus | 100% | 100% | 100% | 100% |  | 100% |
| TiO₂ +Zn 25,000 ppm | 2,000 ppm E. coli | 99.42% | 99.35% | 99.88% | 99.89% | 99.84% | 99.74% |
|  | 3,000 ppm E. coli | 98.88% | 99.56% | 99.28% | — | — | 99.24% |
|  | 4,000 ppm E. coli | 99.35% | 99.59% | 99.56% |  |  | 99.50% |

Table 4 shows an examination result of the antimicrobial activity experiment according to a concentration of the titanium oxide ($TiO_2$).

TABLE 4

|  |  | Experimental conditions | | | | | | |
|---|---|---|---|---|---|---|---|---|
|  |  | 2 hr | | | 4 hr | | | |
| Classification |  | First | Second | Average | First | Second | Third | Average |
| Cu 2000 ppm + Zn 500 ppm | E. coli | 100% | 100% | 100% | 100% | 100% | 100% | 100% |
|  | S. aureus | 100% | 100% | 100% | 100% | 100% | 100% | 100% |
|  | S. typhimurium | 100% | 99.95% | 99.98% | 100% | 99.98% | 99.99% | 99.99% |
|  | K. pneumoniae | 100% | 99.88% | 99.94% | 99.91% | 100% | 100% | 99.97% |
|  | L. monocytogenes | 100% | 99.88% | 99.94% | 100% | 99.99% | 99.98% | 99.99% |
| Cu 2000 ppm + Fe 500 ppm | E. coli | 100% | 100% | 100% | 100% | 100% | 100% | 100% |
|  | S. aureus | 100% | 100% | 100% | 100% | 100% | 100% | 100% |
|  | S. typhimurium | 99.97% | 100% | 99.99% | 100% | 99.98% | 99.99% | 99.99% |
|  | K. pneumoniae | 100% | 100% | 100% | 99.98% | 100% | 100% | 99.99% |
|  | L. monocytogenes | 100% | 100% | 100% | 99.98% | 100% | 100% | 99.99% |
| Cu 2000 ppm + Ag 500 ppm | E. coli | — | — | — | 100% | 100% | — | 100% |
|  | S. aureus | — | — | — | 100% | 100% | — | 100% |
|  | S. typhimurium | — | — | — | 99.97% | 100% | — | 99.99% |
|  | K. pneumoniae | — | — | — | 100% | 99.96% | — | 99.98% |
|  | L. monocytogenes | — | — | — | 100% | 100% | — | 100% |

Table 5 shows a result of the antimicrobial activity experiment according to a concentration of the titanium oxide/copper.

TABLE 5

| TiO₂ concentration | Cu concentration | Strain | | |
|---|---|---|---|---|
|  |  | E. coli | K. pneumoniae | L. monocytogenes |
| 8000 | 1000 | 100% | 98.45% | 99.77% |
|  | 1500 | 100% | 99.38% | 99.94% |
|  | 2000 | 100% | 99.55% | 99.96% |
|  | 2500 | 100% | 100% | 100% |
| 10000 | 2000 | 100% | 100% | 100% |
|  | 3000 | 100% | 100% | 100% |
| 15000 | 1800 | 100% | 100% | 100% |
|  | 2500 | 100% | 100% | 100% |
|  | 3200 | 100% | 99.95% | 100% |
| 16500 | 2000 | 100% | 99.87% | 99.94% |
| 17000 | 2500 | 100% | 99.99% | 99.99% |
| 20000 | 2000 | 100% | 99.88% | 99.92% |
|  | 3000 | 99.95% | 99.95% | 99.33% |
| 21000 | 2000 | 100% | 99.93% | 99.77% |
| 22000 | 2500 | 100% | 99.75% | 99.17% |
| 25000 | 2000 | 100% | 98.97% | 98.82% |

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A refrigerator comprising:
a cabinet having a storage compartment;
a door connected to the cabinet, and configured to open and close the storage compartment;
a sterilizing device installed at a wall surface of the storage compartment; and
a fan installed at the wall surface of the storage compartment, and configured to cycle air in the storage compartment through the sterilizing device,
wherein the sterilizing device comprises:
a case;
a light source assembly which is installed inside the case to emit visible rays; and
a filter assembly comprising:
a photocatalytic filter installed inside the case corresponding to a front of the light source assembly and configured to react with the visible rays emitted from the light source assembly to remove germs; and
a deodorizing filter configured to absorb odor contained in the air passing through the photocatalytic filter, wherein the light source assembly comprises:
a substrate portion which is disposed to be inclined at a predetermined angle greater than 0° and less than 90° with respect to a horizontal line equally dividing the photocatalytic filter in the case; and
a plurality of light emitting elements which are arranged on the substrate portion at predetermined intervals to discharge the visible rays, wherein the fan is parallel to the filter assembly, and wherein air is drawn through the filter assembly before being drawn into the fan,
wherein the case comprises:
a rear case configured to be attached to the wall surface of the storage compartment;
a front case attached to the rear case;
a guide ring detachably coupled to the front case;
a front frame detachably coupled to the front case;
a front cover detachably coupled to the front frame; and
a rear frame provided between the front case and the rear case and configured to support the filter assembly.

2. The refrigerator of claim 1, wherein the light emitting elements comprise an LED element which emits the visible rays having a wavelength of 400 to 760 nm.

3. The refrigerator of claim 2, wherein the LED element comprises a chip-on-board type LED element.

4. The refrigerator of claim 1, wherein the photocatalytic filter comprises:
a first photocatalytic filter which is located at a location farthest away from the light source; and
a second photocatalytic filter which is located at a location closest to the fan,
wherein the deodorizing filter is disposed between the first photocatalytic filter and the second photocatalytic filter.

5. The refrigerator of claim 4, wherein the deodorizing filter comprises:
a first deodorizing filter which is located at a rear of the first photocatalytic filter; and
a second deodorizing filter which is located between the first deodorizing filter and the second photocatalytic filter.

6. The refrigerator of claim 4, wherein a distance between the light emitting element and the second photocatalytic filter is within a range of 3 to 10 mm.

7. The refrigerator of claim 6, wherein the distance between the light emitting element and the second photocatalytic filter is 9 mm.

8. The refrigerator of claim 1, wherein an inclined angle of the substrate portion is within a range of 0 to 45 degrees.

9. The refrigerator of claim 8, wherein the inclined angle of the substrate portion is 25 degrees.

10. The refrigerator of claim 1, wherein a photocatalytic agent coated on the photocatalytic filter comprises a copper-titanium oxide ($CuTiO_2$).

11. The refrigerator of claim 1, wherein the rear case comprises a fixing rib and an elastic support rib provided opposite each other across the rear case, and the substrate portion is configured to be supported between the fixing rib and the elastic support rib.

12. A refrigerator comprising:
a cabinet having a storage compartment;
a door connected to the cabinet and configured to open and close the storage compartment;
a sterilizer provided at a wall surface inside the storage compartment; and
a fan provided adjacent to the sterilizer and configured to cycle air from the storage compartment through the sterilizer, wherein the sterilizer comprises:
a case;
a cover connected to the case and forming a suction port between the cover and the case;
a light source which is installed inside the case to emit visible rays; and
a filter comprising:
at least one photocatalytic filter installed inside the case and configured to react with the visible rays emitted from the light source; and
at least one deodorizing filter provided adjacent to the at least one photocatalytic filter, wherein the light source comprises:
a substrate which is inclined at a predetermined angle greater than 0° and less than 90° with respect to a horizontal line equally dividing the photocatalytic filter in the case; and
a plurality of light emitting elements which are arranged on the substrate at predetermined intervals and face the at least one photocatalytic filter,
wherein the case comprises:
a rear case configured to be attached to the wall surface of the storage compartment;
a front case attached to the rear case;
a guide ring detachably coupled to the front case;
a front frame detachably coupled to the front case; and
a rear frame provided between the front case and the rear case and configured to support the filter.

13. The refrigerator of claim 12, wherein the cover is configured to block the plurality of light emitting elements from being visible to an outside of the refrigerator.

14. The refrigerator of claim 12, wherein the fan is parallel to the filter and the cover.

15. The refrigerator of claim 12, wherein the at least one photocatalytic filter comprises:
a first photocatalytic filter located at a location farthest away from the light source; and
a second photocatalytic filter which is located at a location closest to the fan,
wherein the deodorizing filter is disposed between the first photocatalytic filter and the second photocatalytic filter.

16. The refrigerator of claim 15, wherein the deodorizing filter comprises:
a first deodorizing filter which is located at a rear of the first photocatalytic filter; and
a second deodorizing filter which is located between the first deodorizing filter and the second photocatalytic filter.

17. The refrigerator of claim 12, wherein the fan is configured to suck air from the storage compartment through the filter and discharge the air into a cooling air duct.

18. The refrigerator of claim 12, wherein the rear case comprises a fixing rib and an elastic support rib provided opposite each other across the rear case, and the substrate is configured to be supported between the fixing rib and the elastic support rib.

* * * * *